US006783503B1

(12) United States Patent
Duda et al.

(10) Patent No.: US 6,783,503 B1
(45) Date of Patent: Aug. 31, 2004

(54) METHOD AND DEVICE FOR TESTING THE RIGIDITY OF BIOLOGICAL TISSUE

(75) Inventors: Georg Duda, Berlin (DE); Jan Seufert, Berlin (DE); Uwe Blücher, Berlin (DE)

(73) Assignee: Karl Storz, GmbH & Co. KG, Tuttlingen (DE)

( * ) Notice: Subject to any disclaimer, the term of this patent is extended or adjusted under 35 U.S.C. 154(b) by 340 days.

(21) Appl. No.: 10/018,948

(22) PCT Filed: Jun. 20, 2000

(86) PCT No.: PCT/DE00/01977

§ 371 (c)(1),
(2), (4) Date: Feb. 11, 2002

(87) PCT Pub. No.: WO00/79272

PCT Pub. Date: Dec. 28, 2000

(30) Foreign Application Priority Data

Jun. 21, 1999 (DE) .......................... 199 29 578

(51) Int. Cl.[7] .............................................. A61B 5/103
(52) U.S. Cl. ...................................................... 600/587
(58) Field of Search ................................ 600/587, 552; 73/800, 806, 807

(56) References Cited

U.S. PATENT DOCUMENTS

| | | | | |
|---|---|---|---|---|
| 5,003,982 A | * | 4/1991 | Halperin | 600/552 |
| 5,246,013 A | | 9/1993 | Frank et al. | |
| 5,265,612 A | | 11/1993 | Sarvazyan et al. | |
| 5,474,070 A | | 12/1995 | Ophir et al. | |
| 5,564,435 A | * | 10/1996 | Steinberg | 600/587 |
| 5,673,708 A | | 10/1997 | Athanasiou et al. | |
| 5,701,913 A | | 12/1997 | McPherson et al. | |
| 5,779,651 A | | 7/1998 | Buschmann et al. | |
| 6,527,716 B1 | * | 3/2003 | Eppstein | 600/309 |
| 6,585,666 B2 | * | 7/2003 | Suh et al. | 600/587 |

FOREIGN PATENT DOCUMENTS

| | | | |
|---|---|---|---|
| DE | 3612312 | 10/1986 | G01N/21/84 |
| DE | 19650992 | 5/1998 | G01N/3/28 |
| DE | 19711516 | 10/1998 | A61B/5/00 |
| EP | 0362616 | 9/1989 | A61B/5/103 |
| GB | 2173896 | 10/1986 | G01N/21/47 |
| GB | 2191006 | 12/1987 | G01N/19/02 |
| WO | 9107657 | 5/1991 | G01N/29/00 |
| WO | 9116003 | 10/1991 | A61B/10/00 |
| WO | 9221023 | 11/1992 | G01N/29/18 |
| WO | 9302619 | 2/1993 | A61B/5/103 |
| WO | 9317622 | 9/1993 | A61B/8/00 |
| WO | 9320752 | 10/1993 | A61B/5/103 |
| WO | 9405993 | 3/1994 | A61B/8/00 |
| WO | 9528880 | 11/1995 | A61B/5/103 |
| WO | 9705825 | 2/1997 | A61B/5/107 |
| WO | 9808073 | 2/1998 | G01N/3/48 |

* cited by examiner

Primary Examiner—Eric F. Winakur
(74) Attorney, Agent, or Firm—Horst M. Kasper

(57) ABSTRACT

The invention relates to a method and a device for the contact-free determination of the mechanical rigidity of hard, as well as soft biological materials (e.g. articular cartilage) in body cavities (e.g. arthroscopically), using a defined jet of liquid. The distance between the measurement device and the measurement surface (e.g. articulation surface) is continuously measured in a predetermined measurement zone by means of an optical method. The inventive solution is suited for measuring the mechanical rigidity of native cartilage, articular cartilage substitute, cartilage deficiency fillings or of other biological materials, and therefore for the user-independent and fast analysis of the quality of regenerated materials as compared to the native starting material.

12 Claims, 1 Drawing Sheet

METHOD AND DEVICE FOR TESTING THE RIGIDITY OF BIOLOGICAL TISSUE

Figure 1:
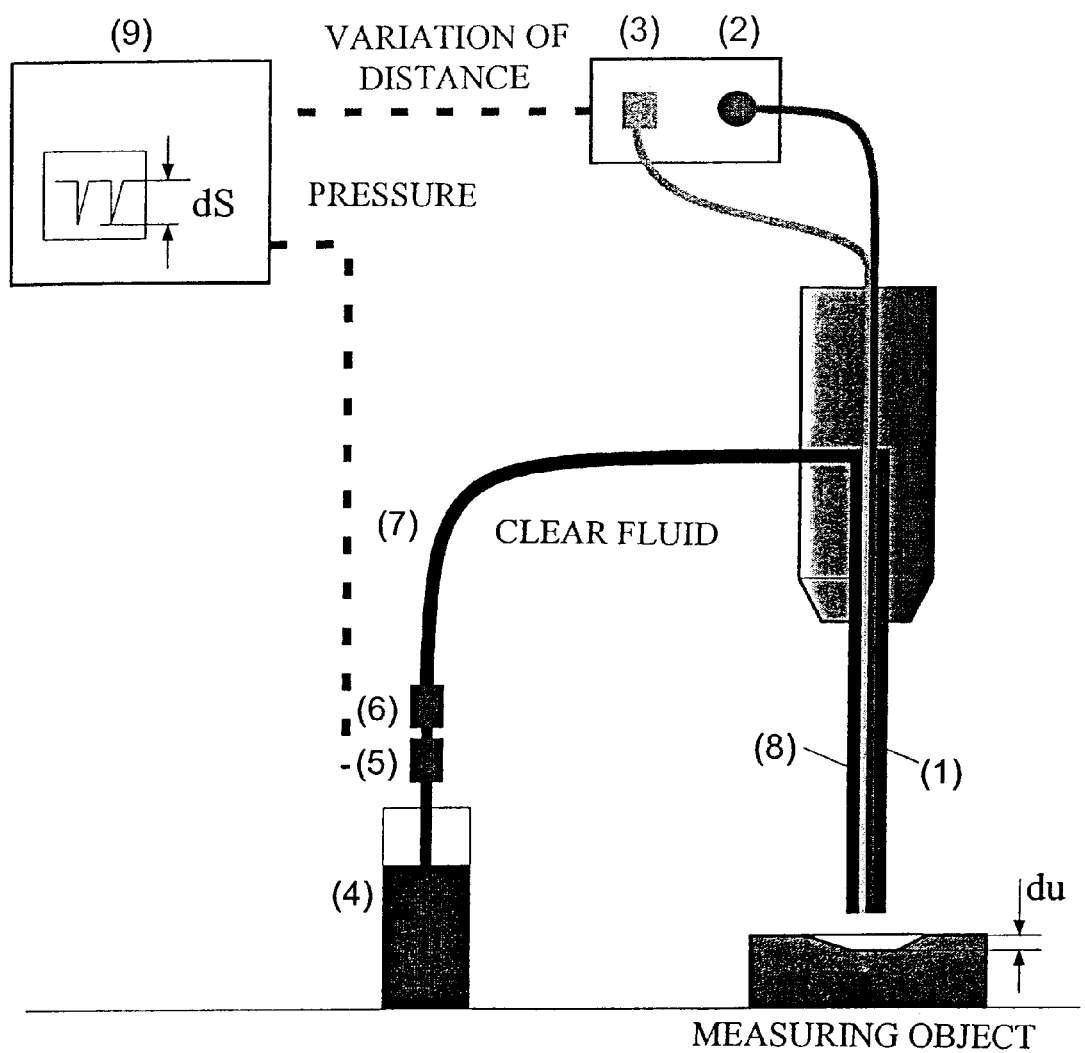

The invention relates to a method and a device for the contact-free determination of the mechanical rigidity of biological tissues in body cavities (also arthroscopically) under a defined jet of liquid. It is suited for measuring the mechanical rigidity of native cartilage, articular cartilage substitute, cartilage deficiency filling, as well as of any other biological tissues. Through comparative measurements, the mechanical quality of the biological materials may be compared to the native material.

For one, the properties of articular cartilage can be determined, for example, optically (arthroscopy), histologically, and by means of imaging methods (magnetic resonance). These methods allow for distinguishing damaged cartilage from sound areas. These methods are moreover used for assessing post-operatively the quality of healing cartilage deficiencies or deficiency fillings. Since articular cartilage is exposed to high loads, its mechanical suitability is an essential criterion for the long-term function of the tissue and the entire articulation. In particular new methods for filling cartilage deficiencies such as, for example, the tissue engineering of articular cartilage, depend on the determination of the mechanical suitability of the deficiency fillings. Though in mere in-vitro tests, the basic suitability of the substitute materials is pre-operatively determinable, more decisive is the mechanical property of the deficiency filling in a post-operative situation.

To date, there exist only few approaches for the post-operative determination of the mechanical suitability of biological tissues (articular cartilage, skin). In the patent specifications U.S. Pat. No. 5,673,708, WO 95/28880, WO 98/08073, WO 97/05825, CA 2161587 and WO 93/02619, mechanical testing instruments are described by means of which the deformation of the cartilage can be determined under a manually applied load.

A disadvantage of these devices and methods, respectively, resides in that altogether relatively high loads are necessary for determining the mechanical rigidity of the articular cartilage. Due to the direct mechanical contact of the test instruments with the articular cartilage, a damage of the regenerated material in particular in reconstructed articulation faces may easily result. Previous devices did not take into account that with manual use, measurement inaccuracies may easily occur due to different test positions and contact forces. The existing methods therewith do not exclude inter-individual variations of the measurement values.

In the patent specifications WO 93/20752 and GB 2191006, the path or path variation is optically determined during a mechanical invasive inspection. This is particularly important with the determination of the relaxation behavior of the cartilage. Similar to the above-mentioned test methods, considerable local test loads arise in the latter method as well. A damage of the newly formed cartilage areas can therewith not be excluded. It may be true that extended testing for determining the relaxation behavior is moreover important in vitro, it is, however, applicable only in a limited manner in a patient measurement.

In the patent specification DE 19711516, U.S. Pat. Nos. 5,779,651, 5,246,013, 5,474,070, WO 94/05993, WO 92/21023, WO 91/07657, WO 93/17622 and U.S. Pat. No. 5,265,612, methods are described, wherein the quality of cartilage or comparable materials is determined by variations in the ultrasonic signals or the electric resistances. A prerequisite for the application of these methods is a direct coupling of the measurement and signal unit to the biological tissue. In particular in arthroscopic examinations, this cannot always be ensured. During surgical operations on a patient, coupling media, which enable a better signal transfer from the measurement device to the biological tissue may be used only in a restricted manner. For this reason, high contact forces are in each case necessary for obtaining the desired signals. With this method, the influence of differing material thicknesses (cartilage thickness) and measurement angles (angles between the incident and the reflected signal path) on the measurement result may not be excluded.

In the patent specifications DE 19650992 A, DE 36123112 A1 and U.S. Pat. No. 5,265,612, methods are described for deforming skin and other soft tissues by defined pressures. A disadvantage of these methods is that only soft samples can be tested, since the deformation is applied by air streams. In addition, in the patent specification DE 36123112 A1, the measurement is not automatically triggered with approximation to the test object. So as to be able to determine the rigidity independent of the respective user, the automatic release of the system at predefined parameters (e.g. distance, pressure), however, is essential.

The invention is based on the task of developing a method and a test device, by means of which the biological properties of biological materials (e.g. articular cartilage) can be determined without causing damage to the biological tissue and without exhibiting strong user-dependent variations in the measurement signal.

This task is solved in that biological samples in body cavities, in particular cartilage, are deformed by a jet of liquid, and that this deformation is optically detected. In a method and by means of a device according to the invention, the distance between the measurement device and the measurement surface (e.g. articulation face) is measured continuously in a predetermined measurement zone with an optical method. If this distance falls below a pre-given value, a clear jet of liquid is directed on the measurement surface at a defined pressure through the feed pipe. The deformation of the test object by the jet of liquid is detected and evaluated by the optical distance measurement system. Starting from a very low load level, the inventive device allows the iterative increase of the load up to a defined, maximally permissible deformation of the sample surface. By means of this proceeding, damages of the sample body (e.g. the articulation face) are supposed to be avoided. From the pressure of the jet of liquid, the tube diameter and the deformation of the articulation surface (distance variation), the rigidity of the cartilage is determined, and is displayed online to the user.

By means of the device realized according to the invention, the mechanical rigidity of biological tissues (e.g. articular cartilage) may also be determined in body cavities (e.g. arthroscopically) without the possibility of resulting in a direct contact of the measurement system with the sample surface, too strong a loading of the sample surface or too strong user-dependent variations of the measurement results.

Surprisingly, it has been found that very soft biological samples (e.g. even reconstructed articulation faces) under a low load (<5 N), as well as very hard samples (e.g. intact cartilage) can be measured. The invention enables the contact-free and user-dependent measurement of biological tissues. The inventive device is simple to handle, of flexible application and easy to operate. Due to the secure function, there does not exist any direct or indirect risk arising from the measurement, neither for the patient nor for the user.

The inventive device is comprised of an optical distance measuring system (FIG. 1: distance alteration) and a unit for applying pressure by means of a clear jet of liquid (FIG. 1: pressure). The optical distance measurement system consists of a light guide (1) (incoming and outgoing line), a light source (2) and a detector (3). The unit for applying pressure by means of a clear liquid consists of a pressure tank (4) having an electric pressure measuring sensor (5), a control unit (6), a feed tube (7), and a feed pipe (8). The data gathering and evaluation ensues via an output unit (9) (FIG. 1).

The inventive method and the inventive device are suited for measuring the rigidity of biological samples in body cavities (e.g. arthroscopic measurement of the rigidity of articular cartilage and regenerated cartilage materials).

The separate components of the device (FIG. 1) interact as follows:

The inventive device is comprised of a combination of known elements and a novel evaluation method (the combination of an optical path measurement and a loading by a jet of liquid), which mutually influence and result in their novel overall action in an advantage of use (synergetic effect) and in the desired success, which resides in that henceforth, a contact-free and user-independent measurement of the mechanical rigidity of biological materials is possible.

| List of reference numerals | |
|---|---|
| 1 | light guide |
| 2 | light source |
| 3 | detector |
| 4 | pressure tank |
| 5 | pressure measuring sensor |
| 6 | control unit |
| 7 | feed tube |
| 8 | feed pipe |
| 9 | evaluation unit |

What is claimed is:

1. A method for measuring the mechanical rigidity of biological samples in body cavities comprising the steps:
    deforming a sample by a jet of liquid to obtain deformations of the sample;
    optically detecting said deformation; and
    determining the mechanical rigidity from said deformation.

2. The method according to claim 1 further comprising
    continuously measuring a distance of a measurement system from a test object at a high resolution;
    determining a falling of the distance below a minimum distance value from the test object; and
    automatically releasing a measurement of the rigidity upon the falling of the distance below the minimum distance from the test object.

3. The method according to claim 1 further comprising
    directing a clear liquid from a pipe to the test object at a defined pressure.

4. The method according to claim 1 wherein said determining comprises
    directly determining the rigidity of the sample from a liquid pressure, a test surface diameter and the deformation; and
    displaying the rigidity of the sample.

5. The method according to claim 1 further comprising
    iteratively increasing an applied load until a defined maximum deformation of a test surface is reached;
    avoiding or keeping damages to the test body at a minimum;
    continuously adjusting applied loads from 0 to 10 N.

6. The method according to claim 1 wherein said deforming and measuring steps are performed by using a measurement time in the millisecond range.

7. The method according to claim 1, wherein the sample is a hard biological material in a body cavity; and further comprising measuring the rigidity of the hard biological material in the body cavity.

8. The method according to claim 1, wherein the sample is a soft biological material in an articulation cavity; and further comprising
    measuring the rigidity of the soft biological material in the articulation cavity.

9. The method according to claim 1 wherein the sample is cartilage and further comprising
    arthroscopically measuring the rigidity of the cartilage.

10. A device for determining the mechanical rigidity of biological samples, comprising
    an optical measurement system;
    means for applying pressure through a clear jet of liquid; and
    an output unit for determining mechanical rigidly based on inputs from said optical measurement system and said means for applying pressure.

11. The device according to claim 10, wherein the optical measurement system is comprised of a light guide (1), a light source (2) and a detector (3).

12. The device according to claim 10, wherein the means for applying pressure through a clear jet of liquid are comprised of a pressure tank (4) having an electric pressure measuring sensor (5), a control unit (6), a feed tube (7) and a feed pipe (8).

* * * * *